United States Patent [19]

Schraga

[11] Patent Number: 5,356,406

[45] Date of Patent: Oct. 18, 1994

[54] ADAPTOR TO FACILITATE INTERCONNECTION OF MEDICINE BOTTLE AND SYRINGE

[76] Inventor: Steven Schraga, 1841 NE. 146 St., North Miami, Fla. 33181

[21] Appl. No.: 2,256

[22] Filed: Jan. 8, 1993

[51] Int. Cl.$^5$ .............................................. A61B 19/00
[52] U.S. Cl. .................... 604/415; 604/403; 215/DIG. 3
[58] Field of Search ............... 604/403, 408, 411, 414, 604/415; 141/330; 215/200, DIG. 3, 316, 317

[56] References Cited

U.S. PATENT DOCUMENTS

| | | | |
|---|---|---|---|
| 4,445,896 | 5/1984 | Gianturco | 604/415 X |
| 4,665,959 | 5/1987 | Takagi | 604/415 X |
| 4,944,736 | 7/1990 | Holtz | 604/415 X |
| 5,125,921 | 6/1992 | Duschek | 604/415 |
| 5,188,620 | 2/1993 | Jepson et al. | 604/415 X |
| 5,230,707 | 7/1993 | Laderoute | 604/415 X |
| 5,247,972 | 9/1993 | Tetreault | 604/414 X |

*Primary Examiner*—Sam Rimell
*Attorney, Agent, or Firm*—Malloy & Malloy

[57] ABSTRACT

For interconnecting a syringe with a barrel and needle to a bottle of medicine wherein the bottle has a generally cylindrical cap with a central target zone of relatively small diameter to be pierced by the needle, wherein the adaptor includes a body having a first end with a truncated cone-shaped mouth converging from the first end and an opposite end with a recess sized to receive the bottle cap, the cone-shaped surface of the mouth being adapted to guide the needle into generally co-axial alignment with the bottle and toward the target zone of the bottle cap.

6 Claims, 1 Drawing Sheet

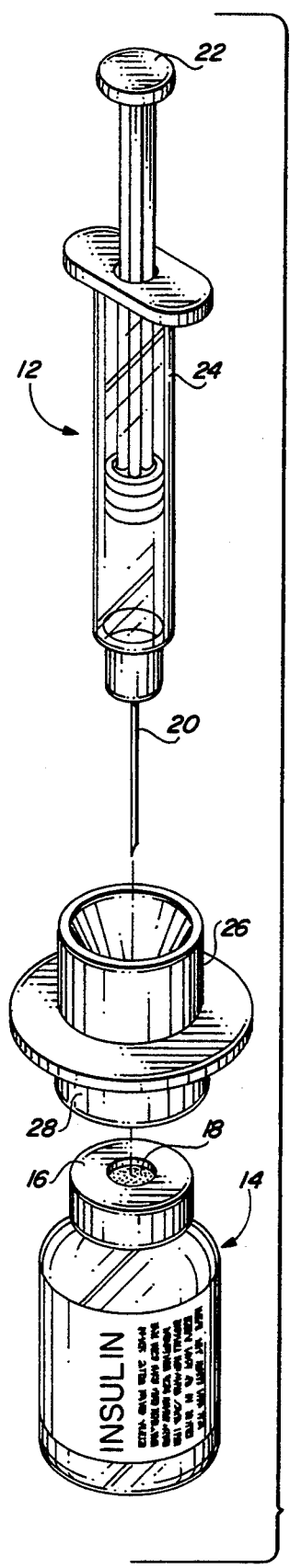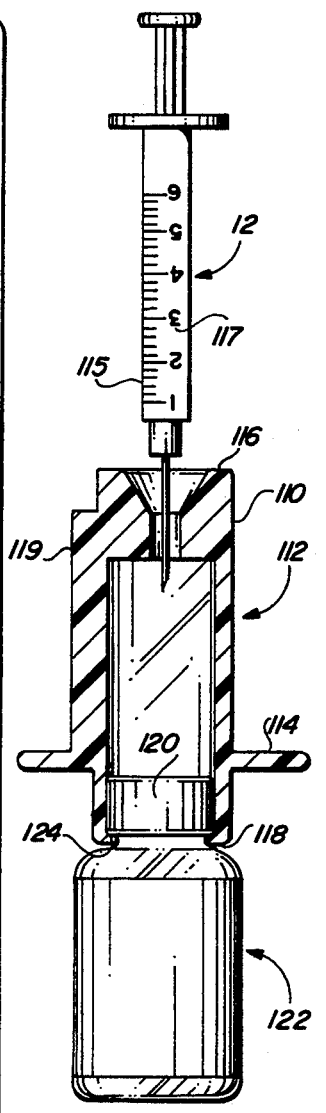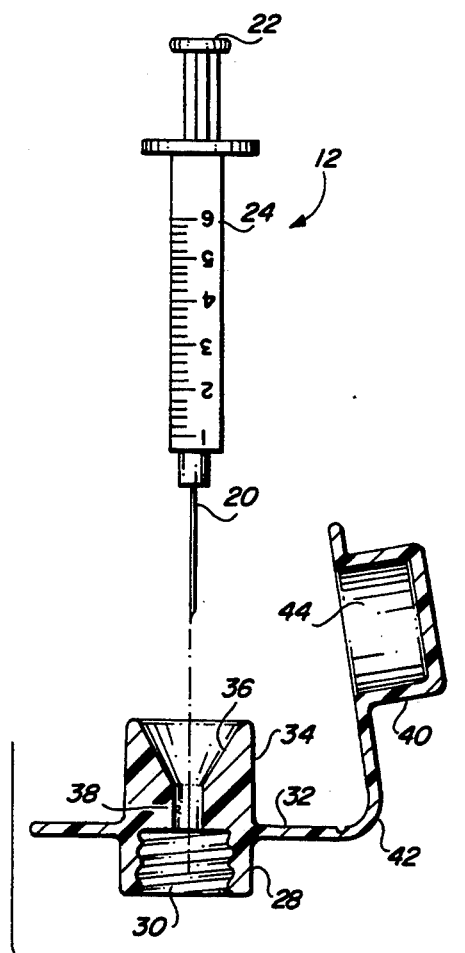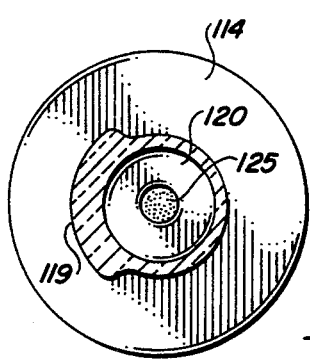
Fig. 1
Fig. 2
Fig. 3
Fig. 4

ADAPTOR TO FACILITATE INTERCONNECTION OF MEDICINE BOTTLE AND SYRINGE

FIELD OF THE INVENTION

This invention is a guide adaptor to be inserted over the cap and needle target zone therein of a medicine bottle to assist a user in piercing the target zone with the needle.

SUMMARY OF THE INVENTION

Some persons regularly use a syringe to inject a dose of medicine, for example, self-administered insulin shots are common by patients. Often such patients are frail, tremble, or have poor eyesight and find it difficult to load their syringe. This is because the typical bottle cap has a relatively small pierceable disk located in the central zone of its cap. This disk is pierced by the needle of the syringe prior to charging the syringe and the small disk presents a small target for the patient. Further, it is difficult, if not impossible, for some patients because often the narrow needle shaft must be pushed co-axially generally into the bottle when the bottle and syringe are tilted or inverted which is a relatively awkward movement with one hand pushing toward the other hand.

This invention is of an adaptor a) which fits over the bottle cap; b) with a bore to face the needle target or central zone of the cap; and c) with a wide mouth to face away from the needle target and a cone-shaped wall surface to guide the needle tip to the needle target in the cap. The adaptor is made of durable molded plastic material and may be transparent.

DESCRIPTION OF THE DRAWINGS

FIG. 1 is an exploded view of the syringe, adaptor and medicine bottle; and

FIG. 2 is an exploded view of the syringe and adaptor, the latter being shown in cross-section.

FIG. 3 is an exploded view of a syringe and medicine bottle with an alternative embodiment of the adaptor, seen in cross-section.

FIG. 4 is a partial view in cross-section taken on the plane indicated by the arrowed line 4—4 of FIG. 3.

DESCRIPTION OF FIRST PREFERRED EMBODIMENT

In FIG. 1, there is shown a syringe 12 and a medicine bottle such as one of insulin which is designated by the numeral 14. The bottle 14 has a cap 16 which is usually about one-half inch in diameter with a central zone or target 18 of pierceable material, which is usually about one-quarter inch in diameter. In use, the needle 20 of the syringe is inserted through the target or central zone 18 ordinarily with the bottle tilted or inverted. Then, the plunger 22 is withdrawn sucking a charge of insulin into the needle barrel 24.

This invention provides an adaptor generally designated by the numeral 26 which is to be disposed between the bottle and the plunger. The adaptor 26 includes an axial passageway. Thus, a skirt 28 with a counter bore as at 30, see FIG. 2, which may be threaded to coact with optional threads on the exterior surface of the cap 16, not shown; or it may be sized for snug receipt over the cap, as in FIG. 1. The adaptor includes a shield 32, preferably, which is for sliding axial movement of the adaptor onto the bottle cap. The adaptor has an upwardly extending truncated cone-shaped defining structure 34 which provides a guiding surface 36 so that the needle is guided to the central bore 38 at its narrowest diameter which is aligned by the adaptor with the target zone 18 of the cap. In use, a frail or trembling patient who has difficulty controlling movements or who has poor eyesight, inserts the adaptor over the bottled cap by pushing on the large diameter shield which makes that movement quite easy to accomplish. In that embodiment of FIG. 2, it is threadably connected. The needle is then inserted into the wide mouth being guided by the cone-shaped surface and structure through the mouth, through the bore, and into the bottle passing through the target zone as axial pressure is applied to the syringe. The central bore is substantially the same diameter as the target zone where it interfaces with it. Thereafter, the syringe and bottle with the adaptor are tilted or inverted and the plunger is withdrawn charging a dose into the syringe barrel to be injected.

In one embodiment to the adaptor, there is provided a cap cover 40 in a hinge flap 42 of relatively thin cross-section which may be used to cover the mouth of the cone-shaped structure. The plastic memory of the plastic tends to keep the cap cover and hinge flap in the normal position shown; but to cover the cap, it may be hingedly moved so that the opening 44 receives the cone defining structure being cooperatively configured and structured for this.

In the embodiment of FIGS. 3 and 4, the syringe 12 and needle end are guided by the truncated cone-shaped walls of the mouth structure 110 of an adaptor 112 which has an annular push flange 114 between one end face 116 and an opposite end face 118. The end face 118 has an opening to receive the cap 120 of the medicine bottle 122. The cap has a pierceable target zone 124. The end face 118 about the opening may include means to engage the bottle cap, such as the annular ridge 124. Between the mouth structure 110 and the end face 118, there is a relatively tubular portion which defines a chamber to receive the syringe barrel which conventionally has dose size indicating indicia therealong, see at 117. The wall of the tubular portion is thickened as at 119 to provide magnifying means for a user with poor eyesight.

While plastic material is described, the adaptor may be of glass paper which can be readily sterilized in conventional medical appliances. It will be appreciated that the tip zone of the barrel 41 of the syringe, which holds the needle, is received in the bore 38 which in use stabilizes and tends to maintain the syringe in co-axial alignment with the adaptor and, accordingly, this structure may be described as means to stabilize and tending to maintain the syringe in co-axial alignment with the adaptor, bottle and the target zone of the bottle cap defined by the pierceable central portion.

While this invention has been shown and described in what is considered to be practical and preferred embodiments, it is recognized that departures may be made within the spirit and scope of this invention which should therefore not be limited except as set forth in the claims which follow and within the doctrine of equivalents.

What is claimed is:

1. For use in charging a dose of medicine through the mouth of a medicine bottle into a syringe having an exterior surface and which syringe includes a barrel and needle extending from the barrel, a medicine bottle cap and a mating tubular adaptor, said cap being sized and configured to engage the medicine bottle and close the bottle mouth and said cap having a central target zone of relatively small diameter in covering relation of a portion of the bottle mouth, said target zone comprising pierceable material to be pierced by the needle to withdraw medicine and charge the syringe barrel with a dose of said medicine, said mating tubular adaptor having a through axial passageway, said adaptor including a) a first end zone with an outer axially facing surface and defining a recessed skirt portion of said passageway extending axially from said outer axially facing surface and into said first zone, said skirt portion being sized and adapted to receive said bottle cap in said recessed skirt position and comprising means to removably fasten said cap to said adaptor and maintain said adaptor and bottle cap in co-axial alignment, b) a second end zone with an outer axially facing surface, said second end zone having a single truncated, cone-shaped recessed portion co-axial with said skirt portion, said truncated, cone-shaped recessed portion converging at a substantially constant slope from an enlarged mouth at the outer axially facing surface of said second end zone with said mouth having a diameter greater than said target zone diameter, c) an intermediate portion between the first and second end zones having a bore interconnecting said cone-shaped recess and said skirt said bore having a diameter substantially equal to said target zone diameter, d) said cone-shaped surface of said recessed portion defining a needle guide means for the distal end of said needle to guide the distal end of the needle to and through said bore and target zone upon the application of a generally co-axially directed force toward the first end to pierce the central target zone of said cap.

2. A medicine bottle cap and mating tubular adaptor as set forth in claim 1 wherein said adaptor is provided by an annular flange between the outer axially facing surface of said first and second end zones to be gripped by a user to apply axial force to push the adaptor onto a bottle cap or to withdraw the adaptor from a bottle cap.

3. A medicine bottle cap and mating tubular adaptor as set forth in claim 1 wherein the adaptor includes a hingedly connected cap cover with a recess, sized and configured to cover and receive the second end zone and receive the cone-shaped recess defining structure on swinging movement from a normal position.

4. A medicine bottle cap and mating tubular adaptor as set forth in claim 1 wherein the first end zone is internally threaded about the through opening.

5. A medicine bottle cap and mating tubular adaptor as set forth in claim 1 wherein said adaptor is of transparent material.

6. A medicine bottle cap and mating tubular adaptor as set forth in claim 1 wherein the adaptor is transparent and is sized and configured to substantially receive the needle barrel therein between the end faces and the adaptor includes magnifying means to enlarge the image of indicia on the barrel.

* * * * *